United States Patent [19]
Hulse et al.

[11] Patent Number: 5,935,136
[45] Date of Patent: *Aug. 10, 1999

[54] OBSTETRICAL VACUUM EXTRACTOR CUP WITH SOFT MOLDED LIP

[75] Inventors: Jerry Dwayne Hulse, Apple Valley; William Henry Wright, Hinkley, both of Calif.

[73] Assignee: Pristech, Inc., Rancho Cucamonga, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/853,422

[22] Filed: May 9, 1997

[51] Int. Cl.⁶ .................................................. A61B 17/42
[52] U.S. Cl. .......................... 606/123; 606/122; 606/119
[58] Field of Search ................................ 606/119–123, 1, 606/106, 110, 127; 604/19, 22, 35

[56] References Cited

U.S. PATENT DOCUMENTS

| | | |
|---|---|---|
| D. 320,855 | 10/1991 | Smith et al. . |
| 667,447 | 2/1901 | Miller . |
| 674,738 | 5/1901 | Mills . |
| 897,289 | 9/1908 | Howell . |
| 1,782,814 | 11/1930 | Froehlich . |
| 2,227,673 | 1/1941 | Price . |
| 2,542,505 | 2/1951 | Gascoigne . |
| 3,202,152 | 8/1965 | Wood et al. . |
| 3,592,198 | 7/1971 | Evans . |
| 3,642,006 | 2/1972 | Wobbe . |
| 3,765,408 | 10/1973 | Kawai . |
| 3,794,044 | 2/1974 | Vennard et al. . |
| 3,988,793 | 11/1976 | Abitbol . |
| 4,014,344 | 3/1977 | Gutierrez . |
| 4,127,632 | 11/1978 | Anger . |
| 4,375,948 | 3/1983 | von Holdt . |
| 4,512,347 | 4/1985 | Uddenberg . |
| 4,620,544 | 11/1986 | O'Neil . |
| 4,633,865 | 1/1987 | Hengstberger et al. . |
| 4,730,617 | 3/1988 | King . |
| 4,794,915 | 1/1989 | Larsson . |
| 4,799,922 | 1/1989 | Beer et al. . |
| 5,019,086 | 5/1991 | Neward .................................. 606/123 |
| 5,163,944 | 11/1992 | Neward .................................. 606/123 |
| 5,224,947 | 7/1993 | Cooper et al. ......................... 606/123 |
| 5,281,229 | 1/1994 | Neward .................................. 606/123 |
| 5,308,321 | 5/1994 | Castro . |
| 5,395,379 | 3/1995 | Deutchman et al. ................... 606/123 |
| 5,507,752 | 4/1996 | Elliott .................................... 606/123 |
| 5,569,265 | 10/1996 | Elliott .................................... 606/123 |
| 5,693,058 | 12/1997 | Cavanagh et al. ..................... 606/119 |
| 5,713,909 | 2/1998 | Lindsay ................................. 606/123 |

FOREIGN PATENT DOCUMENTS

| | | |
|---|---|---|
| 0083328 | 7/1983 | European Pat. Off. . |
| 0527431 | 2/1993 | European Pat. Off. . |
| 1087487 | 2/1955 | France . |
| 3535-055 | 10/1985 | Germany . |

OTHER PUBLICATIONS

O'Grady et al., "Vacuum Extraction in Modern Obstetric Practice," pp. 13–21 (The Parthenon Publishin Group, Inc., New York, NY 1995).

*Primary Examiner*—Glenn K. Dawson
*Attorney, Agent, or Firm*—Leydig, Voit & Mayer, Ltd.

[57] ABSTRACT

The obstetrical vacuum extractor includes a vacuum cup molded of a first, relatively rigid material, with a lip of a second, relatively soft material secured along the basal opening. An elongated hollow stem which may be coupled to a vacuum source communicates with the interior and, accordingly, the basal opening of the vacuum cup. The first, relatively rigid material of the cup is preferably substantially transparent so that the physician may readily monitor the condition of the fetal scalp throughout delivery.

21 Claims, 3 Drawing Sheets

OBSTETRICAL VACUUM EXTRACTOR CUP WITH SOFT MOLDED LIP

TECHNICAL FIELD OF THE INVENTION

The present invention relates to an apparatus for facilitating the delivery of a child during childbirth, and more specifically relates to vacuum extractors for use during childbirth.

BACKGROUND OF THE INVENTION

During childbirth, the birth mother is sometimes unable to deliver the child without assistance. In some cases, all that is required is for a nurse, midwife, or attending physician to push down on the birth mother's upper abdomen when she bears down during delivery. In other cases, it is necessary for a physician to perform a cesarean section. For those cases in between the two extremes, some sort of intermediate assistance is often required. Such intermediate assistance generally entails the use of some sort of device to aid in the delivery of the child. These devices may likewise be required to assist a physician during particularly difficult cesarean sections.

One example of such a device is forceps. Forceps, however, tend to be bulky and difficult to operate. In addition, the use of forceps, at the very least, is uncomfortable for the mother and child and risks injury to both.

An alternative device to forceps is a vacuum extractor device, like the one described in U.S. Pat. No. 3,202,152. Such a device comprises a cup, which is placed onto the child's head. The device further comprises an elongated hollow stem, which is used to position the cup onto the child's head and through which vacuum pressure is introduced into the cup. The introduction of vacuum pressure into the cup results in suction between the cup and the child's head. The resultant suction is then used to extract the child from the birth canal by pulling in an appropriate direction on some sort of gripping device coupled to the vacuum extractor. A similar device is manufactured and sold by PrisTech, Inc. of Cucamonga, Calif.

Although vacuum extractor devices, like the one manufactured and sold by PrisTech, are widely used, the relatively flexible edge of the cup, which facilitates the formation of a good seal between the cup and the child's head, could, due to its relative thinness, abrade or injure the child or mother. U.S. Pat. Nos. 5,163,944 and 5,281,229 disclose vacuum extractors which attempted to address this potential problem, by lining the cup with a second cup formed of a soft, pliable material, which, when assembled, wraps around the edge of the cup. Thus, the first cup provided the relatively rigid structure of the extractor cup while the second cup provided a soft, relatively friendly contact with the child's head. While this vacuum extractor design reduced the possibility abrasion or injury to maternal tissues and the child by cushioning the contact between the vacuum extractor cup and the adjacent tissue, the design was not without its disadvantages. Given that the soft material from which the liner is formed is opaque, the liner occludes vision through the cup. Accordingly, the liner may make it difficult to visually determine if the cup is properly positioned on the child's head or to visually monitor the fetal tissue during delivery to ensure that the amount of suction is appropriate. In addition, if the vacuum extractor is not used properly, the liner may roll off the edge of the cup.

The present invention seeks to overcome the problems of the prior art. Accordingly, it is an object of the present invention to provide a vacuum extractor, which offers the advantages attendant an extractor having a liner, without compromising visibility through the cup and without risking the liner rolling off the edge of the cup. Another object of the present invention is to provide a softer contact between the extractor and child. These and other objects and advantages of the present invention will become apparent from the disclosure herein.

BRIEF SUMMARY OF THE INVENTION

The present invention provides an obstetrical vacuum extractor comprising a vacuum cup, which is substantially in the shape of a bell with an outwardly flaring edge and a basal opening. A hollow stem adapted for connecting with a vacuum source communicates with the inner cavity and basal opening of the cup. The cup is also provided with at least one handle to facilitate maneuvering of the cup during delivery. In accordance with the invention, the extractor further comprises a secondary lip, which is molded from a relatively soft elastomeric material, and is secured on the outwardly flaring edge of the vacuum cup. The relatively soft lip presents a friendly edge to the maternal and fetal tissue as the cup is positioned and during delivery. Further, because the relatively soft second material is disposed only along the edge of the cup, the physician can better observe the interaction between the cup and the child's head. Accordingly, the physician can readily observe whether the cup is properly positioned and if the level of suction is appropriate.

Preferably, the edge of the vacuum cup adjacent the basal opening includes a structure which enhances the attachment of the molded lip. While various designs may be appropriate, the vacuum cup may include one or more protrusions, such as annular ridges, which extend about the periphery of the outwardly flaring edge of the cup. The ridges provide additional gripping surfaces for the softer material of the secondary molded lip.

Alternately, the flaring edge of the cup may be provided with one or more bores which extend through the edge of the cup. The bores are disposed about the periphery of the flaring edge, preferably at substantially regular intervals. When the secondary lip is molded to the flaring edge of the cup, the elastomeric material flows into the bores and along both the inner and outer surfaces of the flaring edge of the cup to secure the secondary lip to the cup.

While the invention will be described in connection with certain preferred embodiments, there is no intent to limit it to those embodiments. On the contrary, the intent is to cover all alternatives, modifications, and equivalents included within the spirit and scope of the invention as defined by the appended claims.

DETAILED DESCRIPTION OF THE INVENTION

Figures 1, 2:
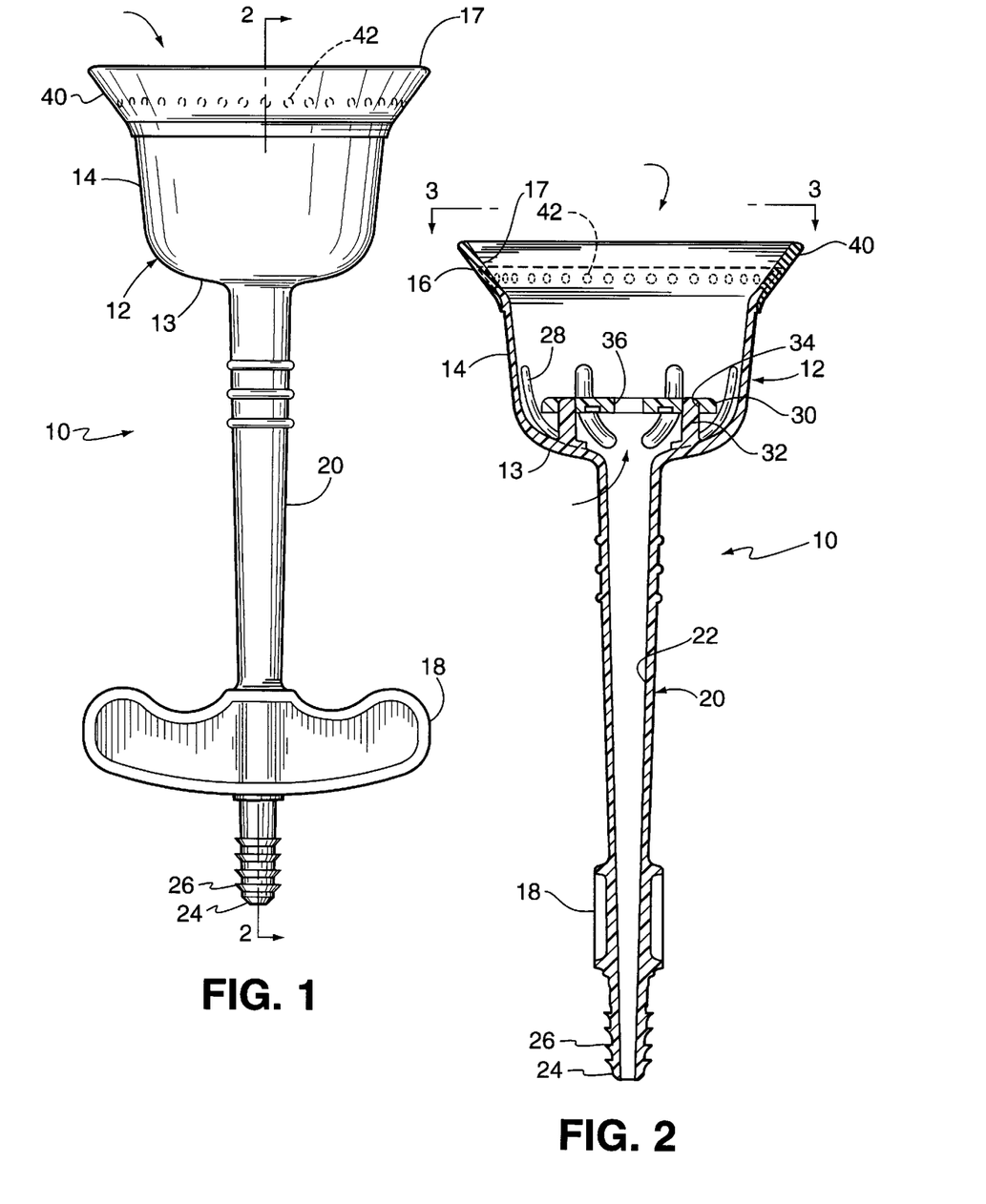
FIG. 1 is a plan view of an obstetrical vacuum extractor constructed in accordance with teachings of the present invention.
FIG. 2 is a cross-sectional view of the obstetrical vacuum extractor of FIG. 1, taken along line 2—2 of FIG. 1.

Turning now to the drawings, there is shown in FIG. 1 an obstetrical vacuum extractor 10 for use in assisted delivery techniques. The vacuum extractor 10 comprises a hollow vacuum cup 12 having a base 13 and an annular side wall 14 which opens into a basal opening 17 for placement against the head of a child. In the embodiment illustrated, the vacuum cup 12 is in the general shape of a bell having an outwardly flaring edge or apron 16 along the basal opening 17. The overall dimensions of the vacuum cup 12 are such that the vacuum cup 12 may be easily inserted into the birth canal and properly positioned onto the child's head.

To facilitate delivery, the obstetrical vacuum extractor 10 is provided with a handle 18, which is coupled to the cup 12 by an elongated stem 20 in the illustrated embodiment. In order to establish a vacuum within the vacuum cup 12 and at the basal opening 17, the elongated stem 20 is hollow, or includes an interior bore 22, which opens into the interior of the hollow vacuum cup 12. To facilitate coupling the hollow elongated stem 20 to a vacuum source (not shown), the outer surface of its distal end is provided with a series of ribs 26 which extend about the circumference of the stem 20. It will thus be appreciated that when a suitable vacuum hose, such as flexible plastic tubing (not shown), is disposed about the distal end 24 of the stem 20, the ribs 26 ensure an airtight connection with the vacuum hose.

It will be appreciated by those skilled in the art that the cup 12 must be sufficiently rigid to withstand the vacuum pressure developed within the cup 12 for extraction of the child during delivery. Typically, the vacuum pressure developed within the cup 12 during use ranges from about 15 to 23 inches Hg (approximately 39–59 cm Hg). Accordingly, the cup 12 must be molded of a sufficiently rigid material and the walls of the cup must be sufficiently thick to withstand the vacuum pressure. A low density polyethylene such as Dow Chemical #722 has been determined to be appropriate. Additional structural strength may be provided by ribs 28 molded into the interior of the side wall 14 of the cup 12.

The illustrated vacuum cup design 12 includes eight ribs 28 disposed equidistant about the interior of the cup 12. The ribs 28 run from the base 13 and along a portion of the side wall 14 of the cup 12. It will be appreciated, however, that the cup could include a greater, or lesser number of ribs, or no ribs, as desired and as allowed by the rigidity of the material from which the cup is molded.

To better distribute the applied vacuum within the cup 12, the vacuum extractor 10 may be provided with a disk 30 disposed subjacent and spaced slightly away from the opening of the bore 22 of the elongated stem 20 into the interior of the hollow vacuum cup 12. The disk 30 is coupled to the base 13 of the cup 12 by a pair of pegs 32 which are received within openings 34 of the disk 30. The ends of the pegs 32 extending through the openings 34 are flattened by sonic welding, or the like to secure the disk 30 to the cup 12. The disk 30 is further provided with a central opening 36 through which the vacuum communicates with the interior of the cup 12. Additionally, the periphery of the disk 30 is slightly smaller than the interior of the vacuum cup 12 (as may be seen in FIG. 2) such that the vacuum flow may also be distributed along the interior of the side wall 14 of the cup.

Preferably, the hollow vacuum cup 12, elongated stem 20 and handle 18 are unitarily molded from a substantially translucent, flexible plastic, such as polyethylene. Those skilled in the art will appreciate that the cup must be sufficiently flexible to be inserted into the birth canal and properly placed on the child's head, yet sufficiently rigid to withstand the vacuum developed within the bore 22 and cup 12. Further, the extractor 10 must be sufficiently rigid to permit the physician to positively manipulate the extractor 10 during extraction.

In accordance with the invention, the extractor 10 is provided with a lip 40 which is molded of a second relatively softer material and is secured along the outwardly flaring edge 16 of the vacuum cup 12. The lip 40 is preferably made of an elastomeric material such as Dynaflex® G2735 by GLS Corporation Thermoplastic Elastomer Division. Those skilled in the art will appreciate that the relatively soft molded lip 40 presents a "friendly" surface for contacting the child's head, as well as maternal tissues. Further, the relatively soft lip 40 is sufficiently flexible to provide a good seal with the child's head and to conform to any irregularities or hair present on the head. Moreover, because the lip 40 presents a relatively soft contact with the child's head, the cup 12 may be molded of a relatively rigid material without compromising the safety, comfort, or performance.

The cup 12 and lip 40 may be molded by conventional molding techniques. For example, the extractor 10 may be molded by dual material molding techniques. That is, the cup 12 and stem 20 may be molded in a conventional mold. With the molded cup and stem remaining in the mold assembly, the portion of the mold adjacent the basal opening 17 may be replaced with a second mold component, and the second material may be introduced into the mold to form the lip 40. Alternately, the lip 40 may be post-molded to a previously molded cup 12 or separately molded and secured to a cup 12.

Preferably, the seal between the lip 40 and cup 12 is enhanced by chemical or mechanical means. In this regard, a portion of the surface of the vacuum cup 12 may be treated with an appropriate adhesive or the like to enhance adhesion between the softer material of the lip 40 and the relatively more rigid material of the vacuum cup 12.

Alternately, mechanical means may be used to enhance adhesion between the lip 40 and the vacuum cup 12. For example, as shown in FIGS. 1–5, the side wall 14 may be provided with one or more bores 42 extending therethrough. In the embodiment illustrated, the cup 12 is provided forty bores 42 which are approximately equally spaced around the outwardly flaring edge 16 and are approximately equally spaced from the end 44 of the cup 12. It will be appreciated, however, that a greater or lesser number of bores 42 of different shapes may be provided and the bores 42 may be disposed at disparate intervals around the side wall 14 and at varied distances from the edge 44 of the cup 12.

Figures 3, 4:
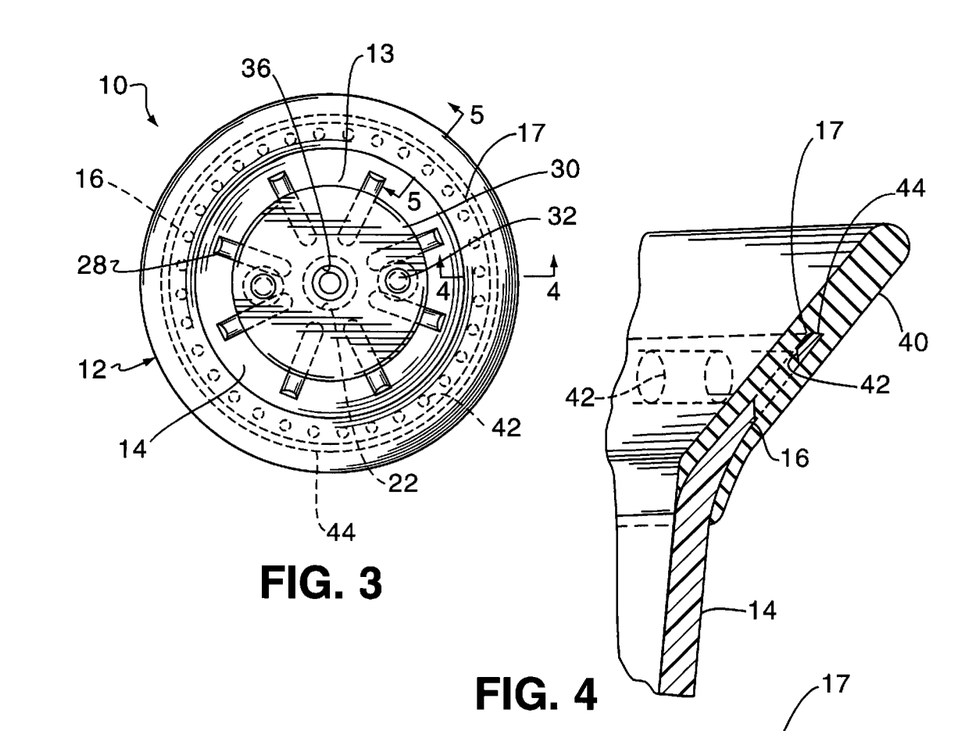
FIG. 3 is a plan view of the obstetrical vacuum extractor of FIG. 1, taken along line 3—3 of FIG. 2.
FIG. 4 is an enlarged, fragmentary cross-sectional view of the obstetrical vacuum extractor of FIG. 1, taken along line 4—4 of FIG. 3.
Figure 5:
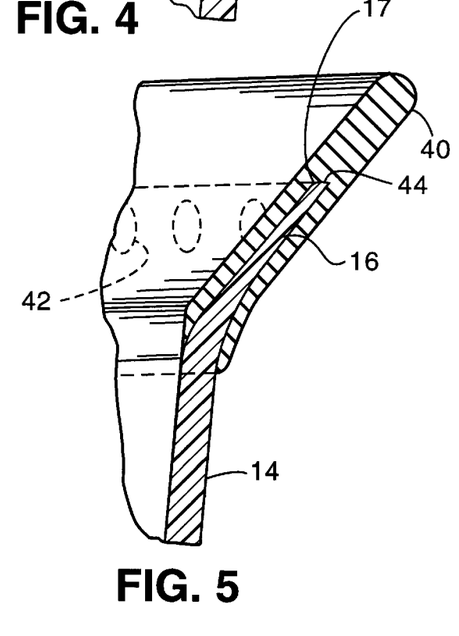
FIG. 5 is an enlarged, fragmentary cross-sectional view of the obstetrical vacuum extractor of FIG. 1, taken along line 5—5 of FIG. 3.

As may be seen in FIG. 4, as the relatively softer material of the lip 40 is molded along the edge 44 and the side wall 14, the material flows in and through the bores 42 to create a mechanical coupling of the lip 40 to the cup 12. As shown in FIGS. 4 and 5, the soft material of the lip 40 extends about 0.35 inch along the outside and inside surfaces of the side wall 14 of the vacuum cup 12 and approximately 0.25 inch beyond the edge 44 of the cup 12. The lip 40 preferably extends on the order of 0.20 to 0.40 inch beyond the edge 44 of the cup 12.

Figures 6, 7:
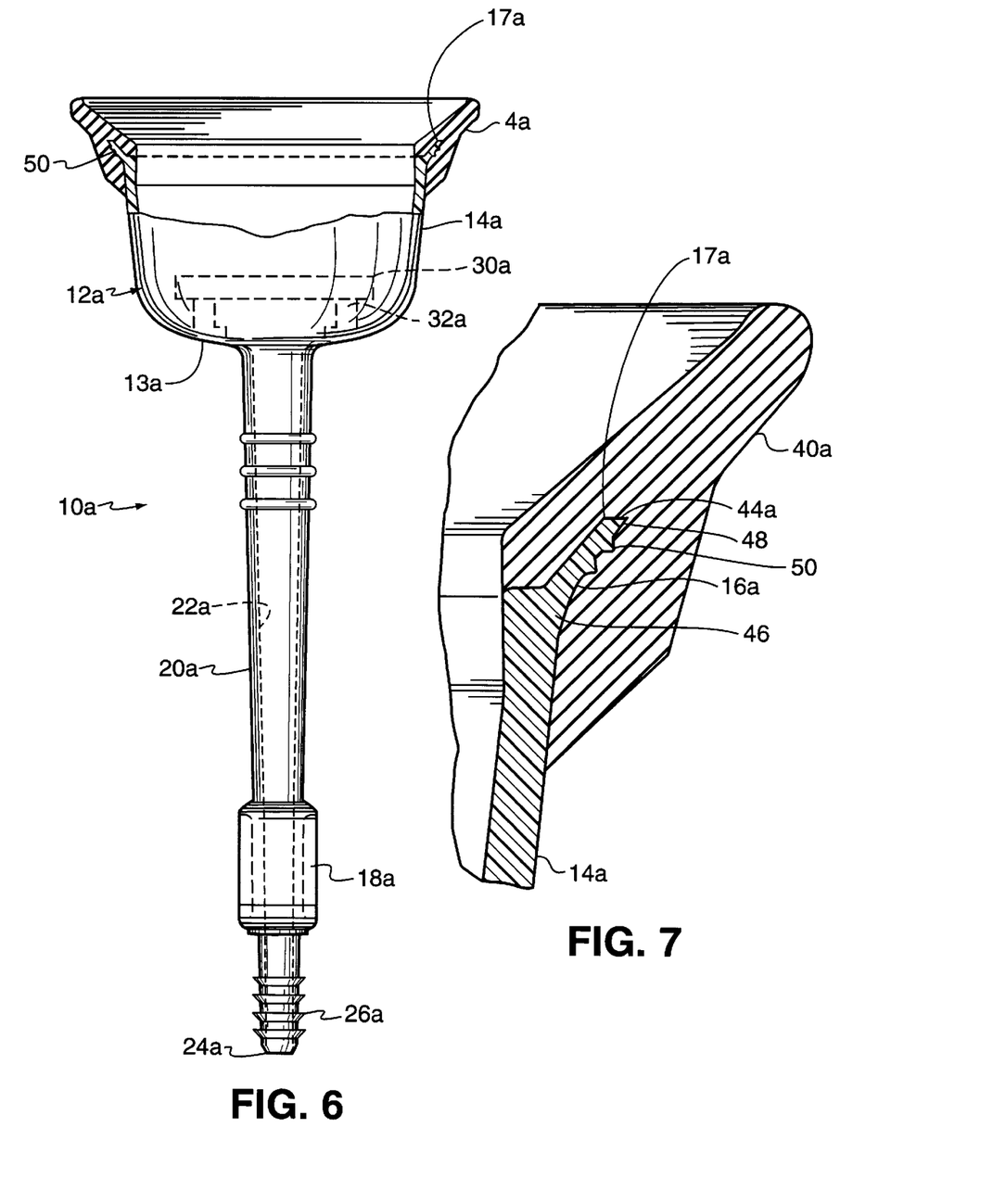
FIG. 6 is a plan view of an alternate embodiment of the invention, partially broken away to show the cross-section of a portion of the cup.
FIG. 7 is an enlarged, fragmentary cross-sectional view of the cup partially broken away in FIG. 6.

An alternate, currently preferred embodiment of the invention is illustrated FIGS. 6 and 7. For clarity, the components of the embodiment shown in FIGS. 6 and 7 which have been previously discussed with regard to the embodiment shown in FIGS. 1–5 will be identified using the same numerals followed by the letter "a." In this embodiment, the side wall 14a has a portion 46 with a substantially uniform thickness from which a reduced thickness portion 48 extends outward. In order to enhance adhesion between the side wall 14a and the lip 40a, a pair of circumferential ridges are disposed along the outer surface of the side wall 14a. It will thus be appreciated by those skilled in the art that the ridges 50 encircling the side wall 14a of the cup 12a increase the surface area for bonding as well as providing an anchor point for the softer molded material of the lip 40a to evenly and consistently bond to the cup 12a during the molding process. In this embodiment, the softer material of the lip 40a extends about 0.38 inch along the outside surface of the side wall 14a, extends only about 0.015 inch along the inside surface of the side wall 14a.

While the vacuum extractor according to the current invention has been described in connection with a bell-shaped cup having an outwardly flaring edge, it will be appreciated that the lip molded of the second softer material may be utilized with alternate cup designs. Moreover, alternate methods for enhancing adhesion and bonding of the second material of the lip to the more rigid material of the cup may be used. For example, alternate designs of projections may be utilized, preferably along the outer surface of the side wall 14. Alternately, a separately molded lip may be bonded to the cup by methods such as adhesion, laser technology, or sonic welding.

In summary, the present invention overcomes disadvantages inherent in currently available obstetrical vacuum extractors. The invention minimizes the potential risk of abrasion or injury to the child or the mother by providing a relatively flexible edge on a relatively rigid cup. Further, the lip may be molded of a relatively opaque material while the cup itself is molded of a relatively transparent material such that the physician may readily monitor the condition of the fetus scalp throughout delivery. Also, inasmuch as the lip is secured, and preferably molded and mechanically coupled, to the side walls of the cup, the risk of the lip rolling off the edge of the cup during improper use is substantially eliminated.

While this invention has been described with emphasis upon preferred embodiments, it will be obvious to those of ordinary skill in the art that the preferred embodiments may be varied. Accordingly, this invention includes all modifications encompassed within the spirit and scope of the appended claims.

What is claimed is:

1. An obstetrical vacuum extractor for placement on a child's head for use during childbirth, the obstetrical vacuum extractor comprising, in combination,
   a vacuum cup formed of a first material, the vacuum cup having a side wall defining a hollow interior cavity, the side wall having a side wall edge forming a cup opening, the vacuum cup further including a vacuum opening communicating with the interior cavity of the vacuum cup and being adapted for connection to a vacuum source;
   a lip formed of a polymeric second material, the second material being flexible relative to the first material, the lip being molded along said side wall edge adjacent the cup opening, the lip having an inner proximal edge terminating substantially at the side wall edge or subjacent the side wall; and
   a handle coupled to the vacuum cup.

2. The obstetrical vacuum extractor of claim 1 wherein the vacuum cup is substantially in the shape of a bell, and the side wall includes a generally outwardly flaring edge, the lip being molded to the outwardly flaring edge.

3. The obstetrical vacuum extractor of claim 1 wherein the lip extends on the order of 0.20 to 0.40 inches beyond the side wall edge.

4. The obstetrical vacuum extractor of claim 1 wherein the cup is substantially transparent such that it does not occlude vision through to the interior cavity of the cup.

5. The obstetrical vacuum extractor of claim 1 wherein the second material is an elastomeric material.

6. The obstetrical vacuum extractor of claim 1 further comprising means for enhancing adhesion of the lip to the vacuum cup.

7. The obstetrical vacuum extractor of claim 1 wherein the side wall further comprises at least one opening extending therethrough, said opening being disposed substantially adjacent the side wall edge, the second material of the lip being molded into the opening to mechanically couple the lip to the vacuum cup.

8. The obstetrical vacuum extractor of claim 7 comprising at least two openings, the openings being circumferentially disposed around the side wall.

9. The obstetrical vacuum extractor of claim 1 further comprising an adhesive applied to a portion of the side wall substantially adjacent the side wall edge such the second material of the lip is molded along the adhesive.

10. The obstetrical vacuum extractor of claim 1 wherein the lip has an inner proximal edge terminating subjacent the side wall.

11. An obstetrical vacuum extractor comprising:
    a vacuum cup substantially in the shape of a bell with an outwardly flaring edge and a cup opening;
    a post-molded lip molded on the outwardly flaring edge of the vacuum cup, the lip having an inner proximal edge terminating substantially subjacent the outwardly flaring edge;
    a hollow, elongated stem integrally formed with the cup and communicating with the cup opening, the distal end of the stem being adapted for connection to a vacuum source; and
    a gripping device coupled to the stem.

12. A method of making an obstetrical vacuum extractor for use during childbirth comprising the steps of:
    molding a hollow vacuum cup of a first material, the cup having a side wall terminating in a distal edge forming a cup opening;
    molding a lip of a polymeric second material along the cup opening, the lip having an inner proximal edge terminating substantially at the distal edge or subjacent the side wall, the second material being flexible relative to the first material.

13. The method of claim 12 wherein the step of molding a hollow vacuum cup of a first material includes the step of molding a substantially transparent cup wall.

14. The method of claim 12 wherein the second material is an elastomeric material.

15. The method of claim 12 wherein the first material is a polyethylene.

16. An obstetrical vacuum extractor for placement on a child's head for use during childbirth, the obstetrical vacuum extractor comprising, in combination,
    a vacuum cup formed of a first material, the vacuum cup having a side wall defining a hollow interior cavity, the side wall having a side wall edge forming a cup opening, the side wall having at least one side wall opening extending therethrough, said side wall opening being disposed substantially adjacent the side wall edge, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening, the second material of the lip being molded into the side wall opening to mechanically couple the lip to the vacuum cup; and a handle coupled to the vacuum cup.

17. The obstetrical vacuum extractor of claim 16 comprising at least two side wall openings, the side wall openings being circumferentially disposed around the side wall.

18. An obstetrical vacuum extractor for placement on a child's head for use during childbirth, the obstetrical vacuum extractor comprising, in combination, a vacuum cup formed of a first material, the vacuum cup having a side wall defining a hollow interior cavity, the side wall having a side wall edge forming a cup opening, the side wall further comprising at least one rib, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening, the second material of the lip being molded to the at least one rib, the lip having an inner proximal edge terminating substantially at the side wall edge or subjacent the side wall; and a handle coupled to the vacuum cup.

19. The obstetrical vacuum extractor of claim 18 wherein the side wall includes an outer substantially circumferential surface, and the at least one rib extends about at least a portion of the circumferential surface.

20. The obstetrical vacuum extractor of claim 18 comprising at least two ribs.

21. An obstetrical vacuum extractor for placement on a child's head for use during childbirth, the obstetrical vacuum extractor comprising, in combination, a vacuum cup formed of a first material, the vacuum cup having a side wall defining a hollow interior cavity, the side wall having a side wall edge forming a cup opening, the side wall further comprising at least one projection extending outwardly from the side wall, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening and being molded along the at least one projection, the lip having an inner proximal edge terminating substantially at the side wall edge or subjacent the side wall; and a handle coupled to the vacuum cup.

* * * * *

(12) EX PARTE REEXAMINATION CERTIFICATE (6461st)
United States Patent
Hulse et al.

(10) Number: US 5,935,136 C1
(45) Certificate Issued: Oct. 7, 2008

(54) OBSTETRICAL VACUUM EXTRACTOR CUP WITH SOFT MOLDED LIP

(75) Inventors: Jerry Dwayne Hulse, Apple Valley, CA (US); William Henry Wright, Hinkley, CA (US)

(73) Assignee: Prism Enterprises, LP

Reexamination Request:
No. 90/005,571, Nov. 24, 1999

Reexamination Certificate for:
| | |
|---|---|
| Patent No.: | 5,935,136 |
| Issued: | Aug. 10, 1999 |
| Appl. No.: | 08/853,422 |
| Filed: | May 9, 1997 |

(51) Int. Cl.
*A61B 17/42* (2006.01)
*A61B 17/46* (2006.01)
*A61D 1/10* (2006.01)

(52) U.S. Cl. .................. 606/123; 606/122; 606/119
(58) Field of Classification Search .................. None
See application file for complete search history.

(56) References Cited

U.S. PATENT DOCUMENTS

| 667,447 A | 2/1901 | Miller |
| 674,738 A | 5/1901 | Mills |
| 897,289 A | 9/1908 | Howell |
| 1,782,814 A | 11/1930 | Froehlich |
| 2,227,673 A | 1/1941 | Price |
| 2,542,505 A | 2/1951 | Gascoigne |
| 3,202,152 A | 8/1965 | Wood et al. |
| 3,522,345 A * | 7/1970 | Olsen .................. 264/273 |
| 3,592,198 A | 7/1971 | Evans |
| 3,642,006 A | 2/1972 | Wobbe |
| 3,765,408 A | 10/1973 | Kawai |
| 3,794,044 A | 2/1974 | Vennard et al. |
| 3,988,793 A | 11/1976 | Abitbol |
| 4,011,819 A * | 3/1977 | Kessler .................. 264/273 |
| 4,014,344 A | 3/1977 | Gutierrez |
| 4,038,359 A * | 7/1977 | Pendleton .................. 264/263 |
| 4,127,632 A | 11/1978 | Anger |
| 4,338,278 A * | 7/1982 | Schultz .................. 264/261 |
| 4,375,948 A | 3/1983 | von Holdt |
| 4,467,930 A | 8/1984 | Schnell et al. |
| 4,512,347 A | 4/1985 | Uddenberg |
| 4,535,827 A * | 8/1985 | Seaford .................. 264/273 |
| 4,620,544 A | 11/1986 | O'Neil |
| 4,632,267 A | 12/1986 | Fowles et al. |
| 4,633,865 A | 1/1987 | Hengstberger et al. |
| 4,730,617 A | 3/1988 | King |
| 4,794,915 A | 1/1989 | Larsson |
| 4,799,922 A | 1/1989 | Beer et al. |
| 4,904,248 A * | 2/1990 | Vaillancourt .................. 604/329 |
| 4,983,160 A | 1/1991 | Steppe et al. |
| 5,019,086 A | 5/1991 | Neward |

(Continued)

FOREIGN PATENT DOCUMENTS

| DE | 3535-055 A | 10/1985 |
| EP | 0083328 | 7/1983 |
| EP | 0527431 | 2/1993 |
| FR | 1087487 | 2/1995 |

OTHER PUBLICATIONS

Gutta–percha on Encylopedia.com 2002, p. 1□□http://www.encyclopedia.com/html/g/guttaper.asp.*

(Continued)

*Primary Examiner*—Beverly M. Flanagan (57) ABSTRACT

The obstetrical vacuum extractor includes a vacuum cup molded of a first, relatively rigid material, with a lip of a second, relatively soft material secured along the basal opening. An elongated hollow stem which may be coupled to a vacuum source communicates with the interior and, accordingly, the basal opening of the vacuum cup. The first, relatively rigid material of the cup is preferably substantially transparent so that the physician may readily monitor the condition of the fetal scalp throughout delivery.

U.S. PATENT DOCUMENTS

| | | | |
|---|---|---|---|
| 5,021,206 | A | 6/1991 | Stoops |
| D320,855 | S | 10/1991 | Smith et al. |
| 5,132,494 | A | 7/1992 | Burton et al. |
| 5,163,944 | A | 11/1992 | Neward |
| 5,224,947 | A | 7/1993 | Cooper et al. |
| 5,246,065 | A | 9/1993 | Huff |
| 5,281,229 | A | 1/1994 | Neward |
| 5,308,321 | A | 5/1994 | Castro |
| 5,375,183 | A | 12/1994 | Edwards et al. |
| 5,395,379 | A | 3/1995 | Deutchman et al. |
| 5,405,467 | A * | 4/1995 | Young et al. .............. 264/273 |
| 5,462,622 | A | 10/1995 | Small et al. |
| 5,507,752 | A | 4/1996 | Elliott |
| 5,569,265 | A | 10/1996 | Elliott |
| 5,626,489 | A | 5/1997 | Marshall et al. |
| 5,693,058 | A | 12/1997 | Cavanagh et al. |
| 5,713,909 | A | 2/1998 | Lindsay |
| 5,833,903 | A * | 11/1998 | Centofante .............. 264/155 |
| 5,842,711 | A | 12/1998 | Legerot |
| 5,957,725 | A | 9/1999 | Bianca et al. |

OTHER PUBLICATIONS

The Columbia Encylopedia, Sixth edition. 2001 Rubber p. 1–3□□wysiwyg://84/http://www.bartleby.com/65/ru/rubber.html□□.*

V. Finderle, "Assisting Delivery Through Use of An Extractor," Gynaecologia, vol. 133, No. 4, pp. 225–230 (Apr. 1952) (Foreign Language Document, Translation Enclosed).

V. Finderle, "Extractor Instead of Forceps," Am. J. Obst. & Gynec., vol. 69, No. 5, pp. 1148–1153 (May 1955).

J. A. Chalmers, "The Ventouse," pp. 1–17 (Lloyd–Luke Medical Books 1971).

M. Hartung, "Multicomponent Injection Molding: New Technology Boosts Versatility," Plastics Technology, vol. 25, No. 10, pp. 65–69 (Sep. 1979).

R. V. Wilder, "Multicomponent Injection Emerges As Strategic Capability," Modern Plastics, vol. 67, No. 9, pp. 65–69 (Sep. 1990).

Vacca, "Handbook of Vacuum Extraction in Obstetric Practice," pp. 1–12 (Edward Arnold, London, 1992).

D. Richmond, "Multi–Color Technique Reveals New Applications," SPE TPEL RETEC Technical Papers, pp. 133–146 (Oct. 1993).

W. Michaeli & S. Brinkmann, "Multi–Component Injection Molding—Influence of Process Parameters on the Adhesion of Rigid–Flexible Combinations," ANTEC Conference Proceedings, vol. 1, pp. 742–746 (1995).

O'Grady et al., "Vacuum Extraction in Modern Obstetric Practice," pp. 13–21 (The Parthenon Publishing Group, Inc., New York, NY 1995).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9, 11, 12, 16, 18 and 21 are determined to patentable as amended.

Claims 2–8, 10, 13–15, 17, 19 and 20, dependent on an amended claim, are determined to be patentable.

New claims 22–44 are added and determined to be patentable.

1. An obstetrical vacuum extractor for placement on a child's head for use during childbirth, the obstetrical vacuum extractor comprising, in combination, a vacuum cup formed of a first material, the vacuum cup having a side wall defining a hollow interior cavity, the side wall having a side wall edge forming a cup opening, the vacuum cup further including a vacuum opening communicating with the interior cavity of the vacuum cup and being adapted for connection to a vacuum source;

a lip formed of a polymeric second material, the second material being flexible relative to the first material, the lip being molded along said side wall edge adjacent the cup opening, the lip having an inner proximal edge *and including an outwardly extending portion* terminating [substantially at] *beyond* the side wall edge or subjacent the side wall, *the lip and the side wall having adjacently disposed surfaces;*

*a bond between the adjacently disposed surfaces of the side wall and the lip;* and a handle coupled to the vacuum cup.

9. The obstetrical vacuum extractor of claim 1 further comprising an adhesive applied to a portion of the side wall substantially adjacent the side wall edge such *that* the second material of the lip is molded along the adhesive.

11. An obstetrical vacuum extractor comprising:

a vacuum cup substantially in the shape of a bell with an outwardly flaring edge and a cup opening;

a post-molded lip molded on the outwardly flaring edge of the vacuum cup, the lip having an inner proximal edge *and including an outwardly extending portion* terminating [substantially subjacent the outwardly flaring edge] *beyond the outwardly flaring edge, the lip and the outwardly flaring edge having adjacently disposed surfaces;*

*a bond between the adjacently disposed surfaces of the side wall and the lip;* a hollow, elongated stem integrally formed with the cup and communicating with the cup opening, the distal end of the stem being adapted for connection to a vacuum source; and a gripping device coupled to the stem.

12. A method of making an obstetrical vacuum extractor for use during childbirth comprising the steps of:

molding a hollow vacuum cup of a first material, the cup having a side wall terminating in a distal edge forming a cup opening;

*injection* molding a lip of a polymeric second material along the cup opening, the lip having an inner proximal edge *and including an outwardly extending portion* terminating [substantially at] *beyond* the distal edge or subjacent the side wall, the second material being flexible relative to the first material.

16. An obstetrical vacuum extractor for placement on a child's head for use during childbirth, the obstetrical vacuum extractor comprising, in combination, a vacuum cup formed of a first material, the vacuum cup having a side wall defining a hollow interior cavity, the side wall having a side wall edge forming a cup opening, the side wall having at least on side wall opening extending therethrough, said side wall opening being disposed substantially adjacent the side wall edge, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cop opening, the second material of the lip being molded into the side wall opening to mechanically couple the lip to the vacuum cup, *the lip including an outwardly extending portion terminating beyond the side wall edge;* and a handle coupled to the vacuum cup.

18. An obstetrical vacuum extractor for placement on a child's head for use during childbirth, the obstetrical vacuum extractor comprising, in combination, a vacuum cup formed of a first material, the vacuum cup having a side wall defining a hollow interior cavity, the side wall having a side wall edge forming a cup opening, the side wall further comprising at least one rib, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening, the second material of the lip being molded to the at least one rib, the lip having an inner proximal edge *and including an outwardly extending portion* terminating [substantially at] *beyond* the side wall edge or subjacent the side wall, *the lip and the side wall having adjacently disposed surfaces;*

*a bond between the adjacently disposed surfaces of the side wall and the lip;* and a handle coupled to the vacuum cup.

21. An obstetrical vacuum extractor for placement on a child's head for use during childbirth, the obstetrical vacuum extractor comprising, in combination, a vacuum cup formed of a first material, the vacuum cup having a side wall defining a hollow interior cavity, the side wall having a side wall edge forming a cup opening, the side wall further comprising at least one projection extending outwardly from the side wall, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening and being molded along the at least one projection, the lip having an inner proximal edge *and including an outwardly extending portion* terminating [substantially at] *beyond* the side wall edge or subjacent the side wall, *the lip and the side wall having adjacently disposed surfaces;* a bond between the adjacently disposed surfaces of the side wall and the lip; and a handle coupled to the vacuum cup.

22. An obstetrical vacuum extractor for placement on a child's head during childbirth and the reduction of pressure within the vacuum extractor relative to an outside atmosphere, the obstetrical vacuum extractor comprising, in combination, a vacuum cup formed of a first material, the vacuum cup having a side wall defining a hollow interior cavity, the side wall having a side wall edge forming a cup opening, the vacuum cup further including a vacuum opening communicating with the interior cavity of the vacuum cup and being adapted for connection to a vacuum source;

a lip formed of a polymeric second material, the second material being flexible relative to the first material, the lip having an inner proximal edge and including an outwardly extending portion terminating beyond the side wall edge or subjacent the side wall, the lip being molded along said side wall adjacent the cup opening leaving substantially no interstices between the lip and the side wall whereby air could pass from the atmosphere between the lip and the side wall to the hollow interior cavity of the vacuum cup; and a handle coupled to the vacuum cup.

23. The obstetrical vacuum extractor of claim 22 wherein the vacuum cup is substantially in the shape of a bell, and the side wall includes a generally outwardly flaring edge, the lip being molded to the outwardly flaring edge.

24. The obstetrical vacuum extractor of claim 22 whrein the lip extends on the order of 0.20 to 0.40 inches beyond the side wall edge.

25. The obstetrical vacuum extractor of claim 22 wherein the cup is substantially transparent such that it does not occlude vision through to the interior cavity of the cup.

26. The obstetrical vacuum extractor of claim 22 wherein the second material is an elastomeric material.

27. The obstetrical vacuum extractor of claim 22 further comprising means for enhancing adhesion of the lip to the vacuum cup.

28. The obstetrical vacuum extractor of claim 22 wherein the side wall further comprises at least one opening extending therethrough, said opening being disposed substantially adjacent the side wall edge, the second material of the lip being molded into the opening to mechanically couple the lip to the vacuum cup.

29. The obstetrical vacuum extractor of claim 28 comprising at least two openings, the openings being circumferentially disposed around the side wall.

30. The obstetrical vacuum extractor of claim 22 further comprising an adhesive applied to a portion of the side wall substantially adjacent the side wall edge such that the second material of the lip is molded along the adhesive.

31. The obstetrical vacuum extractor of claim 22 wherein the lip has an inner proximal edge terminating subjacent the side wall.

32. An obstetrical vacuum extractor for placement on a child's head during childbirth and the reduction of pressure within the vacuum extractor relative to an outside atmosphere, the obstetrical vacuum extractor comprising:

a vacuum cup substantially in the shape of a bell with an outwardly flaring edge and a cup opening, said vacuum cup having a hollow interior cavity;

a post-molded lip molded on the outwardly flaring edge of the vacuum cup, the lip having an inner proximal edge and including an outwardly extending portion terminating beyond the outwardly flaring edge, the post-molded lip being molded along said outwardly flaring edge adjacent the cup opening leaving substantially no interstices between the lip and the outwardly flaring edge whereby air could pass from the atmosphere between the lip and the outwardly flaring edge to the hollow interior cavity of the vacuum cup;

a hollow, elongated stem integrally formed with the cup and communicating with the cup opening, the distal end of the stem being adapted for connection to a vacuum source; and a gripping device coupled to the stem.

33. A method of making an obstetrical vacuum extractor for placement on a child's head during childbirth and the reduction of pressure within the vacuum extractor relative to an outside atmosphere, the method comprising the steps of:

molding a hollow vacuum cup of a first material, the cup having a side wall terminating in a distal edge forming a cup opening; and molding a lip of a polymeric second material along the cup opening, the lip having an inner proximal edge and including an outwardly extending portion terminating beyond the distal edge or subjacent the side wall, the second material being flexible relative to the first material, the lip being molded along said side wall distal edge adjacent the cup opening leaving substantially no interstices between the lip and the side wall whereby air could pass from the atmosphere between the lip and the side wall to the hollow interior cavity of the vacuum cup.

34. The method of claim 33 wherein the step of molding a hollow vacuum cup of a first material includes the step of molding a substantially transparent cup wall.

35. The method of claim 33 wherein the second material is an elastomeric material.

36. The method of claim 33 wherein the first material is a polyethylene.

37. An obstetrical vacuum extractor for placement on a child's head during childbirth and the reduction of pressure within the vacuum extractor relative to an outside atmosphere, the obstetrical vacuum extractor comprising, in combination, a vacuum cup formed of a first material, the vacuum cup having a side wall defining a hollow interior cavity, the side wall having a side wall edge forming a cup opening, the side wall further comprising at least one rib, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening, the second material of the lip being molded to the at least one rib, the lip having an inner proximal edge and including an outwardly extending portion terminating beyond the side wall edge or subjacent the side wall, the lip being molded along said side wall adjacent the cup opening and along the at least one rib leaving substantially no interstices between the lip and the side wall whereby air could pass from the atmosphere between the lip and the side wall to the hollow interior cavity of the vacuum cup; and a handle coupled to the vacuum cup.

38. The obstetrical vacuum extractor of claim 37 wherein the side wall includes an outer substantially circumferential surface, and the at least one rib extends about at least a portion of the circumferential surface.

39. The obstetrical vacuum extractor of claim 37 comprising at least two ribs.

40. An obstetrical vacuum extractor for placement on a child's head during childbirth and the reduction of pressure within the vacuum extractor relative to an outside atmosphere, the obstetrical vacuum extractor comprising, in combination, a vacuum cup formed of a first material, the vacuum cup having a side wall defining a hollow interior cavity, the side wall having a side wall edge forming a cup opening, the side wall further comprising at least one projection extending outwardly from the side wall, the vacuum cup further including a vacuum opening communicating with the interior cavity of the vacuum cup and being adapted for connection to a vacuum source;

a lip formed of a polymeric second material, the second material being flexible relative to the first material, the lip being secured along said side wall edge adjacent the cup opening and being molded along the at least one projection, the lip having an inner proximal edge and including an outwardly extending portion terminating beyond the side wall edge or subjacent the side wall, the lip being molded along said side wall adjacent the cup opening leaving substantially no interstices between the lip and the side wall whereby air could pass from the atmosphere between the lip and the side wall to the hollow interior cavity of the vacuum cup; and a handle coupled to the vacuum cup.

41. A method of making an obstetrical vacuum extractor for use during childbirth comprising the steps of:

molding a hollow vacuum cup of a first material, the cup having a side wall terminating in a distal edge forming a cup opening;

molding a lip of a polymeric second material along the cup opening, the lip having an inner proximal edge and including and outwardly extending portion terminating beyond the distal edge or subjacent the side wall, the second material being flexible relative to the first material, the lip and the side wall having adjacently disposed surfaces; and creating a bond between the adjacently disposed surfaces of the side wall and the lip.

42. The method of claim 41 wherein the step of molding a hollow vacuum cup of a first material includes the step of molding a substantially transparent cup wall.

43. The method of claim 41 wherein the second material is an elastomeric material.

44. The method of claim 41 wherein the first material is a polyethylene.

* * * * *